US009345435B1

(12) United States Patent
DelAguila

(10) Patent No.: US 9,345,435 B1
(45) Date of Patent: May 24, 2016

(54) ESOPHAGEAL INTRODUCER

(71) Applicant: Cesar DelAguila, Nacogdoches, TX (US)

(72) Inventor: Cesar DelAguila, Nacogdoches, TX (US)

(73) Assignee: Cesar Del Aguila, Nacogdoches, TX (US)

(*) Notice: Subject to any disclaimer, the term of this patent is extended or adjusted under 35 U.S.C. 154(b) by 95 days.

(21) Appl. No.: 14/164,234

(22) Filed: Jan. 26, 2014

(51) Int. Cl.
*A61B 5/00* (2006.01)
*A61B 5/02* (2006.01)
*A61B 17/02* (2006.01)

(52) U.S. Cl.
CPC ............... *A61B 5/687* (2013.01); *A61B 17/02* (2013.01)

(58) Field of Classification Search
CPC ........................................................ A61B 5/00
USPC ........................................ 600/184–246, 114
See application file for complete search history.

(56) References Cited

U.S. PATENT DOCUMENTS

| 3,913,565 | A |  | 10/1975 | Kawahara |  |
|---|---|---|---|---|---|
| 4,195,624 | A |  | 4/1980 | Douglas |  |
| 5,279,610 | A | * | 1/1994 | Park et al. | 606/108 |
| 5,390,661 | A |  | 2/1995 | Griffith |  |
| 6,474,332 | B2 | * | 11/2002 | Arndt | 128/200.26 |
| 2003/0213492 | A1 | * | 11/2003 | Alfery et al. | 128/207.14 |
| 2008/0103508 | A1 |  | 5/2008 | Karakirum |  |
| 2009/0030284 | A1 |  | 1/2009 | Cole |  |
| 2012/0283513 | A1 | * | 11/2012 | Leeflang et al. | 600/114 |
| 2013/0006057 | A1 |  | 1/2013 | Pastron |  |

OTHER PUBLICATIONS

Lee, L., Weightman WM. Laryngoscopy for in the sniffing position compared to the extension-extension position. Anesthesia.Apr. 2008; 63 (4): 375-8.
El-Orbany M. Woelick H. Salem MR. Head and neck position for direct laryngosoopy. Anesth Analg. Jul. 2011 113(1): 103-9.
Blondheim DS. Levi D Marmor AT. Mild sedation before transesophageal echo induces significant hemodynamic and repiratory depression. Echocardiography. Apr. 2004 21(3): 241-5.
Greenland KB, Edwards MJ, Hutton NJ, Chalilis VJ, Irwin MG, Sleigh JW. Changes in airway configuration with different head and neck positions using magnetic resonance imaging of normal airways: a new concept with possible clinical applications. Br J Anesth. Nov. 2010; 105(5):603-90.
Reuss C, Triester S, Lynch J, Height R. Esophageal Overtube Facilitation of Transesophageal Echocardiography in Patients with Previously Difficult Esophageal Intubation. J Am Soo Echocardiography. Mar. 2007 vol. 20 (2):285-9.
Wells C. Fleischer D. Overtubes in Gastrointestinal Endoscopy. Am J Gastroenterol 2008; 103: 745-752.

* cited by examiner

*Primary Examiner* — Christopher Beccia

(57) ABSTRACT

An esophageal introducer is provided which facilitates the passage of medical probes into the esophagus or gastric cavity. It consists of an introduced tube 12 made of collapsible elastomeric material 21 with a flexible laminated steel at the bottom 20. The proximal opening is attached to a bite block 10. The distal end continues with an extension of the laminated steel 20a that tapers to a tip with a 45 degree bend 16. This extension is covered with elastomeric material 21a that overlaps the distal tip creating a flat soft end 19. Prior to insertion the introducer body is bended 20-30 degrees 17, the tip is advanced till it makes contact with the posterior pharyngeal wall FIG. 3a.
Further pressure will advance the tip effortlessly, sliding on the posterior esophageal wall that is an anatomic continuation of the posterior pharyngeal wall. FIG. 3b, 3c.

19 Claims, 6 Drawing Sheets

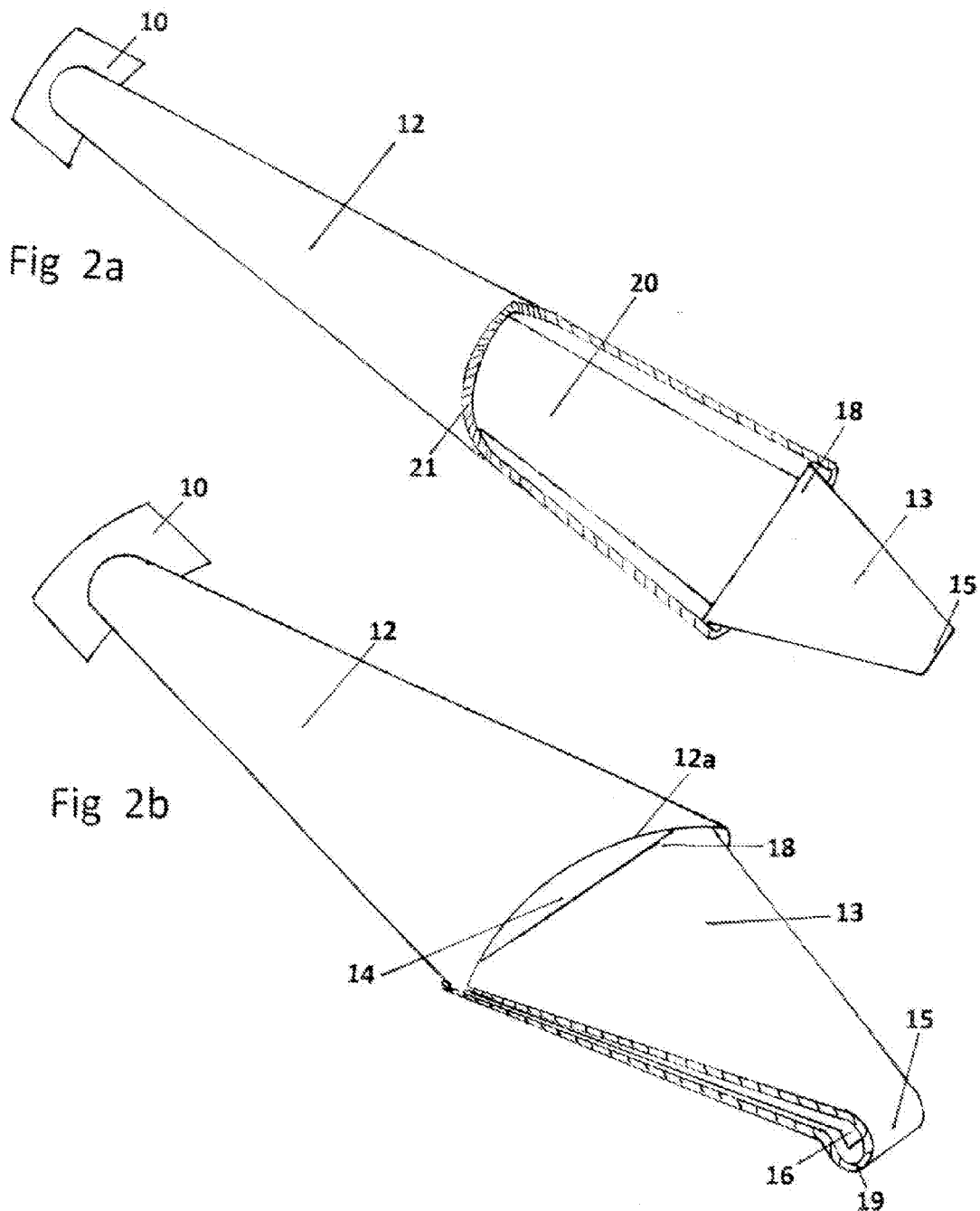

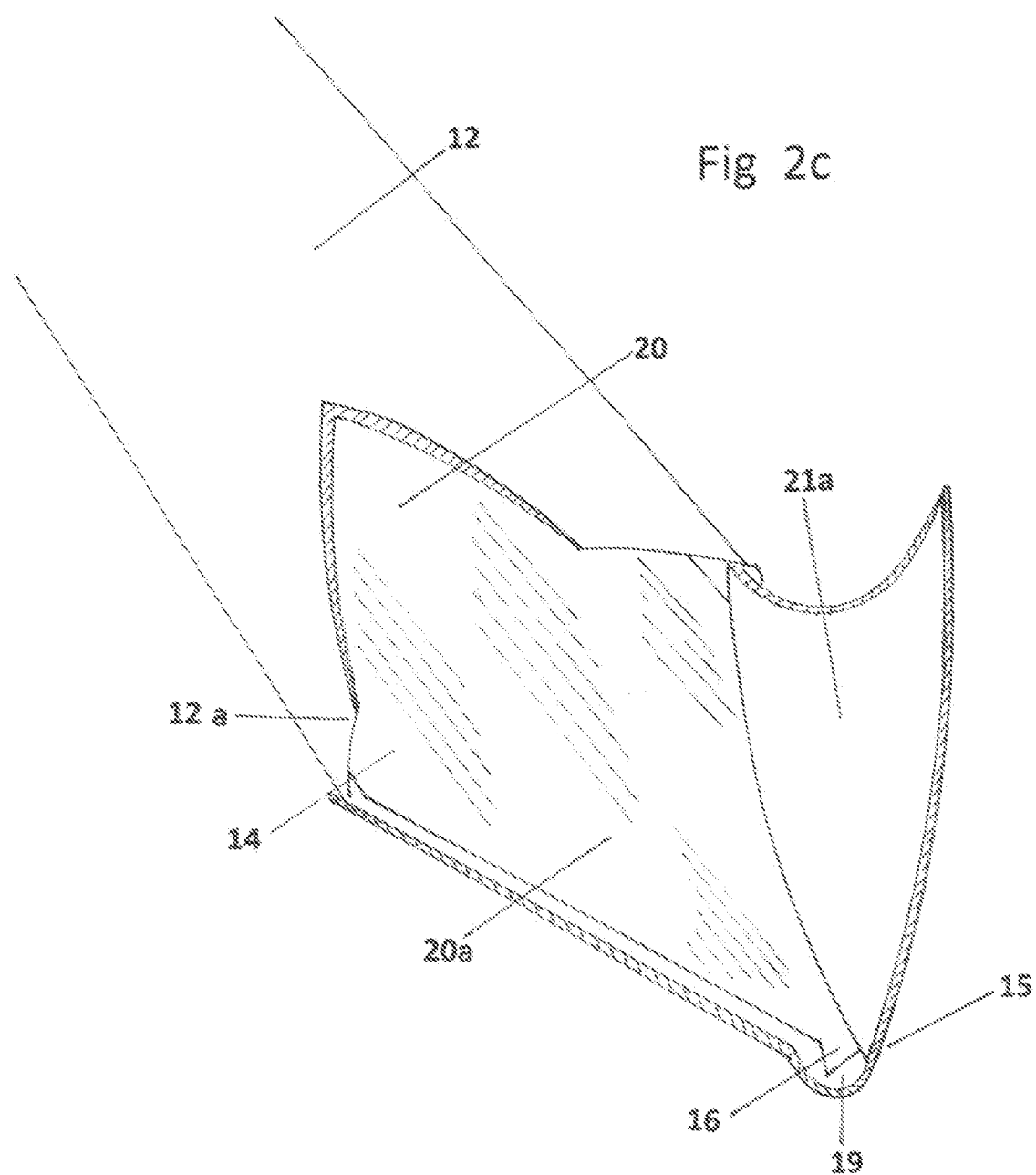

ESOPHAGEAL INTRODUCER

CROSS REFERENCE APPLICATIONS

NONE

FEDERALLY SPONSORED RESEARCH

NONE

SEQUENCE LISTING OR PROGRAM

NONE

BACKGROUND

1. Field

This application relates to medical instruments used to reach the esophagus through the mouth for diagnostic or therapeutic purposes.

2. Prior Art

Echocardiography is considered as one of the most significant advancements in medical science of the past century.

Nonetheless a consecrated tool in the specialty, it found substantial limitations inherent to the physics of the instrumentation. The resolution of the images, an indispensable feature in the accuracy of any imaging modality, is drastically diminished by the distance of the interrogation point and the ultrasound transducer. The interposition of air also renders the tool useless since ultrasound waves cannot be transmitted through this media. Therefore, obesity, COPD and senile emphysema, are conditions that present an insurmountable challenge to the conventional technology. Patients in the intensive care unit undergoing mechanical ventilation also present outstanding difficulties for the transthoracic echocardiographic evaluation. Trans esophageal echocardiography is a technology that came to overcome the above mentioned limitations and became irreplaceable, in circumstances in which ultrasound images of the heart were required and a conventional transthoracic approach was suboptimal. In addition, new indications came to solidify the need for this technology as are the investigation of valvular vegetations, atrial clots, and the presence of patent foramen ovale in addition to intraoperative monitoring of valvular surgery, precardioversion evaluation, among others. One of the most commonly encountered problems with this technology is the passage of the probe in to the esophagus. A substantial limitation is the physical constraint that requires a bulky shape and size of the distal probe that harbors the ultrasound crystals and mechanical components.

Figure 4:
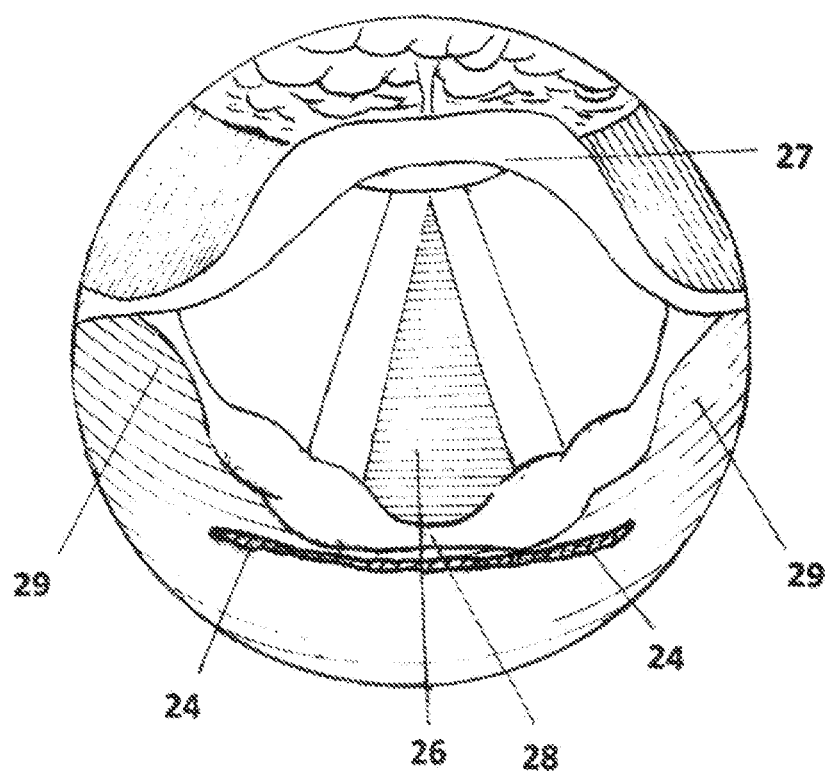

The passage of such an element through the orophagyngeal area presents self-evident difficulties. The gag reflex is a life preserving characteristic that makes any attempts to introduce any bulky material into the esophagus a very difficult endeavor. Not unexpectedly, the process of passing of the probe through the throat in to the esophagus is the origin of most the complications of the procedure namely, trauma to the larynx or pharynx, bleeding, pain, abscess formation not to mention the discomfort of withstanding such an unnatural procedure. In an attempt to circumvent these limitations, sedation is included routinely. There is no a particular protocol or method to warrant an easy passage of the TEE probe into the esophagus. The probe is supposed to advance straight down into the mid portion of the posterior pharyngeal wall and then by further pressing on the posterior wall the tip should advance into the esophagus since the posterior pharyngeal wall continues seamlessly with the posterior esophageal wall. This process is tainted, by the fact that the procedure is done blindly since the probe has to pass beyond the line of sight behind the base of the tongue, before entering into the esophagus. In addition, esophageal opening 24, FIG. 4 is a virtual space that only opens up during the deglutition process. Therefore, near 100% of the cross sectional area at the level of esophageal opening 24, FIG. 4 is comprised by glottis 26, epiglottis 27 and pyriform sinuses 29. In the usual protocol the transesophageal probe is pushed blindly against a closed esophagus assuming that the tip is positioned medially so it will fall against the esophageal opening. Many times, the patient is called to help by trying to swallow the probe, in very unfriendly circumstances. In addition, a particular disadvantage of transesophageal probes in comparison with gastric endoscopes is that the distal angulation does not follow an even curvature but it has an inflection point caused by the unyielding nature of the rigid case in the distal 7 cm of the probe. This unavoidable physical constrain is the reason of the much more difficult negotiation of the TEE probe into the esophagus. Other techniques used by physicians like using the fingers to manipulate the distal end of the probe or the use of laryngoscopes to visualize the esophageal opening are also used, albeit at the cost of increased discomfort and potential complications for patients and operators.

Even more, the introduction of conscious sedation to decrease the anxiety of the procedure adds another component of risk and the more difficult the passage of the probe is, the more sedation is needed. Depending of the level of sedation, the patient loses the ability to defend itself against the aggression of the procedure and cases of tracheal intubation and aspiration have been well documented. Previous attempts have been made to create a device that would facilitate the esophageal intubation for transesophageal echocardiograms, however none of them were able to gain acceptance.

Douglas U.S. Pat. No. 4,195,624, filed Jun. 9, 1978, describes a device to facilitate the insertion of an endoscope into the esophagus made of a flexible elastomer and a solid tapered tubular end into which the tip of the probe is inserted. Embodiment only add a tapered end to the endoscope but does not facilitate the location of the esophageal opening and obliges to use a large volume tubular structure as the tool to find the opening which seriously limit the accuracy of the maneuvers when the tip is behind the tongue.

Griffith U.S. Pat. No. 5,390,661, filed Feb. 3, 1993, presents an introducer with a pilot member and a coaxially fitting sheath. The first embodiment is a device similar to a medical endoscope steerable fitting into a sheath that can be used as the pilot member. Albeit the steer ability is an attractive feature, the cost makes it a less desirable device.

Kawahara U.S. Pat. No. 3,913,565, filed Apr. 25, 1974, describes a guide tube to insert instruments into body cavities. Albeit this device was also for esophageal introduction, is merely a flexible tube to guide an endoscope but does not facilitate the localization of the esophageal opening.

Park U.S. Pat. No. 5,279,610, filed Nov. 6, 1992, describes a three component structure with a semi rigid sheath, a coaxial introducer guide and a dilator tip. Again, it does not provide a straightforward method that allows the introducer guide to find the esophageal opening.

Pastron US patent application 2013/0006057, filed Dec. 29, 2011, describes a device to keep the mouth open during procedures done through the mouth. It serves as a tongue depressor that goes as far as the posterior aspect of the tongue. However, even though it provides a light source and passage ways for catheters, this does not facilitate the introduction of medical probes into the esophagus. Besides, the device aims to decrease the gag reflex but it places the distal portion thereof on the posterior aspect of the tongue where the gag reflex is mostly located.

Karakurum US patent 2008/0103508 A1 filed Nov. 1, 2006, describes an esophageal overtube with a basket at the distal end for retrieval of impacted food bolus. It does not describe an easy way into the esophagus but with an endoscope.

Balbierz US patent application 2008/008726, filed Jul. 17, 2008, describes an esophageal overtube that is preferably inserted with the guidance of an endoscope or through a guide wire that itself has to be inserted through an endoscope. Albeit the tube is designed to facilitate the repeated insertion of endoscopes during the same procedure, It still requires an endoscope for its initial insertion.

Cole US patent application 2009/0030284A1, filed Jul. 17 2008, describes a large introducer tube as part of an assembly for intragastric procedures. Preferably it has to be inserted with the use of an endoscope, alternatives embodiments include a wire that has to be inserted with an endoscope and then the tube has to have a tapered adaptor to follow the wire. A bougie with a snug fit at the distal end and a umbrella type device at the distal end are ways to introduce the tube without the need of an endoscope, but the difficulties finding the esophageal opening without direct visualization remains unsolved as with prior devices.

SUMMARY OF THE INVENTION

A simple, non-reusable, economical, easy to build and to use device is provided that allows esophageal access effortlessly at a first attempt, without the need for patient participation in the process.

In general, the present device is in essence a collapsible sheath to facilitate the introduction of probes or tubes into the esophagus for medical purposes.

The device is a simple structure comprising of three components, a proximal bite block; a device well known to people familiar with the art. A body of flexible and fully collapsible elastomeric tube with a stiff laminated strip component attached at the bottom of the fully collapsible elastomeric tube. This element provides skeletal consistency while allowing great anteroposterior flexibility. A third component, that is the continuation of the laminated strip component, protrudes about 3 cm beyond the distal opening of the fully collapsible elastomeric tube. This strip is covered with elastomeric material.

The bite block is attached to the flexible fully collapsible elastomeric tube. It has a smooth tapering towards the distal end with a diameter that allows the passage of most medical instruments used in the trade. The elastomeric introducer tube is fully collapsed while is positioned in the esophagus. Albeit quite flexible is able to maintain its uniform shape thanks to the stiff laminate attached to its bottom, to allow guidance during the passage of medical probes. Thanks to its fully collapsible nature, it has a very low profile. This greatly improves patient's tolerance and minimizes trauma to the mucosal surfaces. The elastomeric material has to be very flexible and malleable, able to collapse under minor pressure, therefore it does not have radial strength.

A particular feature that greatly facilitates the use of this embodiment is the design of the distal component. The laminate strip element in the elastomeric tube continues beyond the distal opening tapering down to a narrow tip. The elastomeric material covering its surface folds over at the tip and creates a cushioned end. This tip makes the initial contact with the posterior pharyngeal wall and then slides down into the esophagus without any maneuvering other than gentle pressure in the proximal end comprised of the bite block.

The inclusion of a semi rigid laminate in the embodiment allows great anteroposterior flexibility without possibility of lateral displacement. This feature is essential to secure positioning of the tip in the middle of the posterior pharyngeal wall. A 20-30 degree angle in the mid portion of the fully collapsible introducer tube, allows the tip of the embodiment to traverse parallel to posterior pharyngeal wall behind the tongue, beyond the line of sight and then into the continuing posterior esophageal wall. This advancement is done effortlessly without forcing the patient into any awkward and uncomfortable swallowing attempts.

DRAWINGS

Figures

Figure 1A:
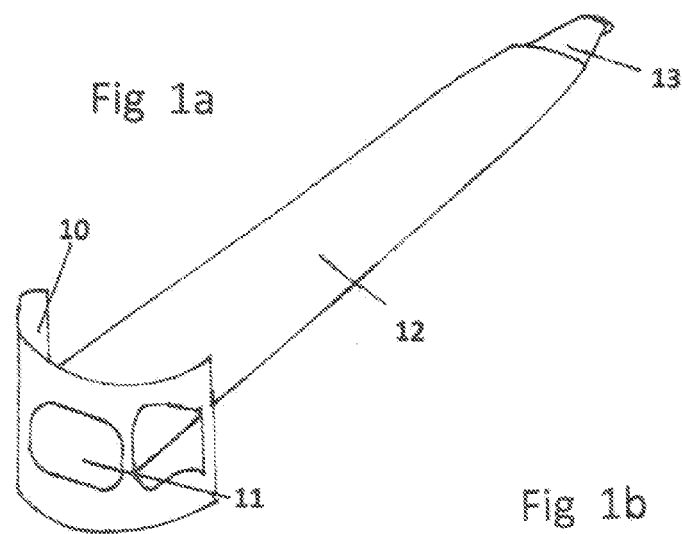

FIG. 1a: Introducer tube and bite block.

Figure 1B:
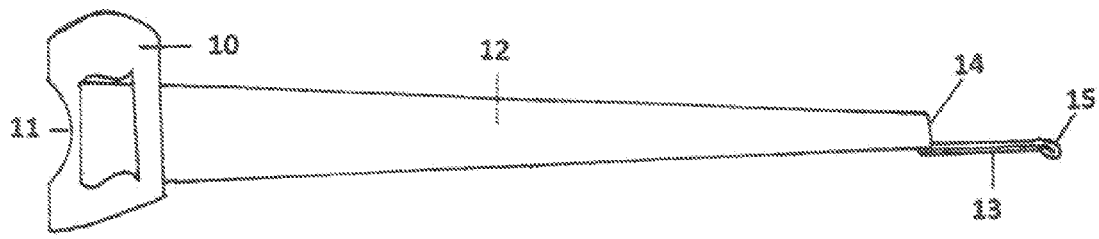

FIG. 1b: Profile of Bite block, introducer tube and Introducer extension.

Figure 1C:
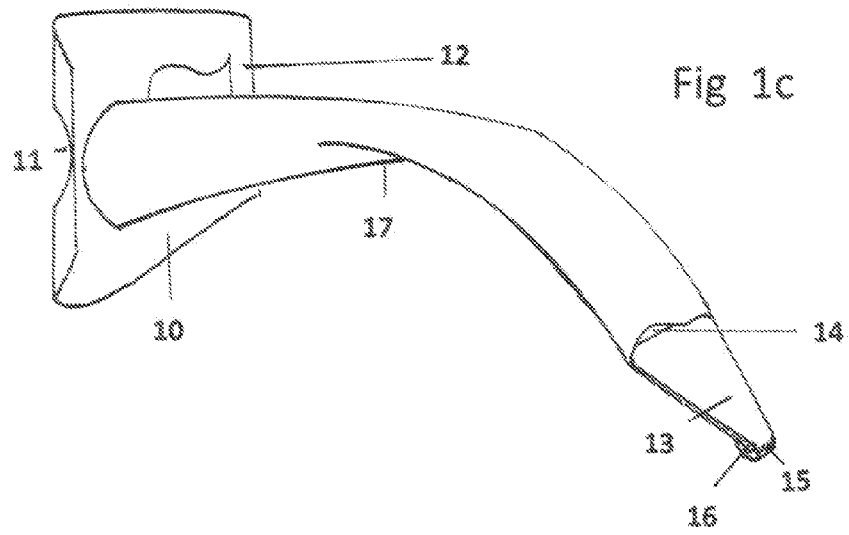

FIG. 1c: Introducer extension and bending of introducer tube prior to insertion.

FIG. 2a: Elastomeric tube cut off detail, showing the steel laminate at the bottom of elastomeric tube and Introducer extension.

FIG. 2b: Distal Introducer tube view and Introducer extension. Detail of Introducer extension tip showing the angulation of steel laminate tip and overlap of elastomeric material.

FIG. 2c: Introducer extension detail showing semirigid laminate extension and elastomeric material display.

Figure 3A:
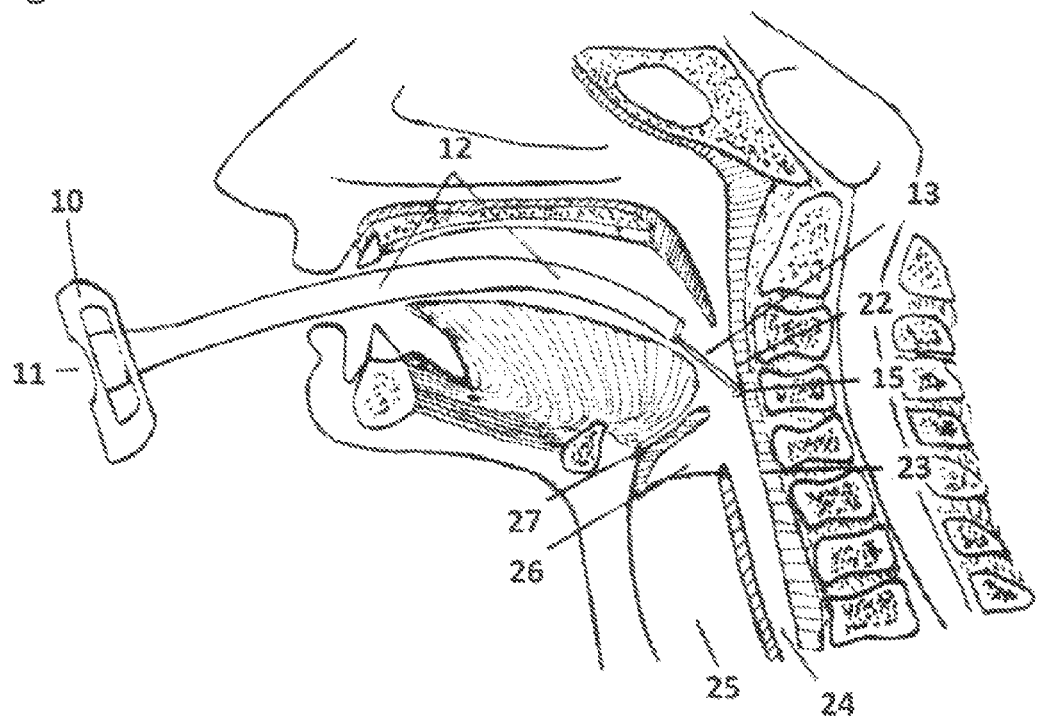

FIG. 3a: Oro pharyngeal esophageal anatomy, introducer position at the beginning of the insertion process.

Figure 3B:
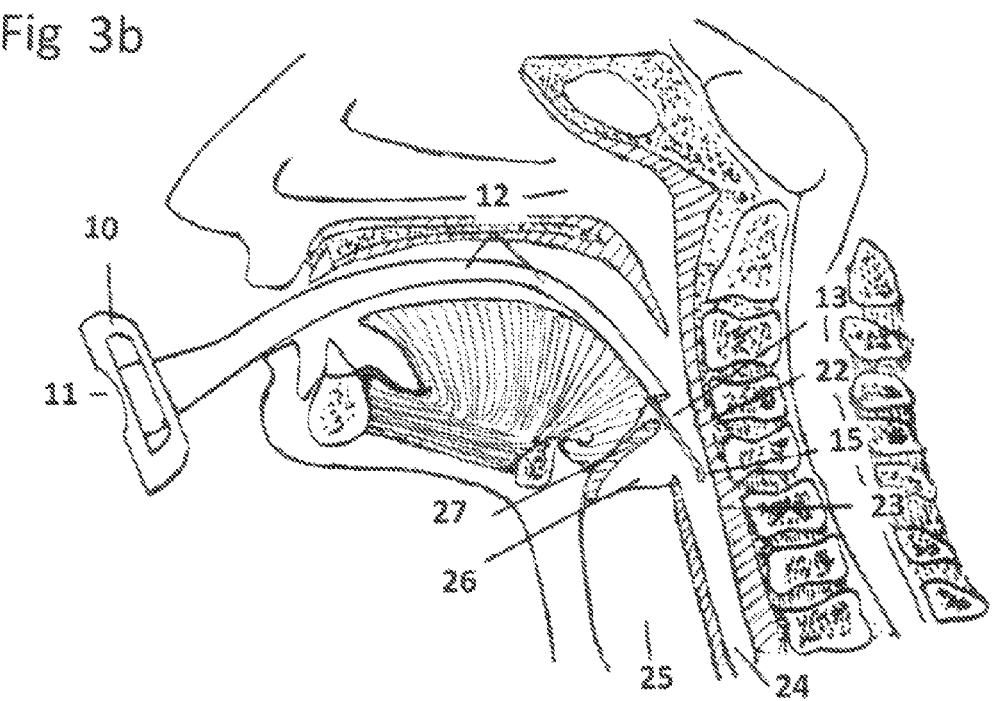

FIG. 3b: Oro pharyngeal esophageal anatomy, further advancement of introducer during the insertion process.

Figure 3C:
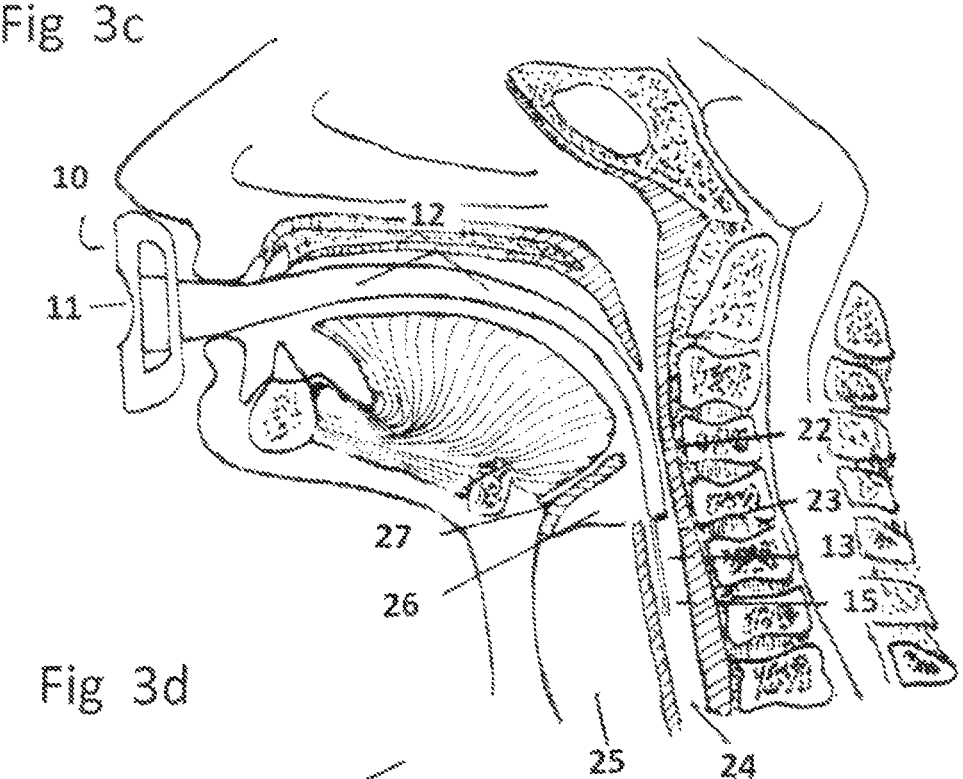

FIG. 3c: Oro pharyngeal esophageal anatomy, final introducer position with distal opening at about interarythenoid notch.

Figure 3D:
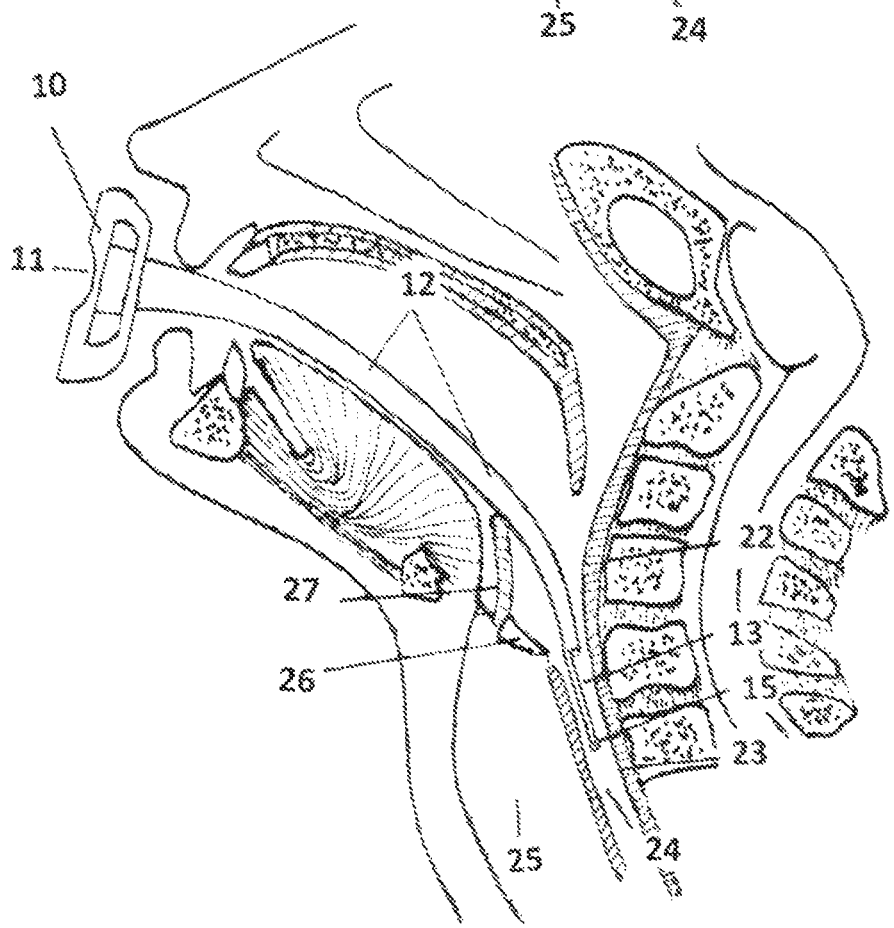

FIG. 3d: Hyperextension of neck with smoothing of oropharyngeal angulation to facilitate passage of probe.

FIG. 4: Glottis and adjacent anatomical structures showing the virtual space slit like esophageal opening.

Figure 5:
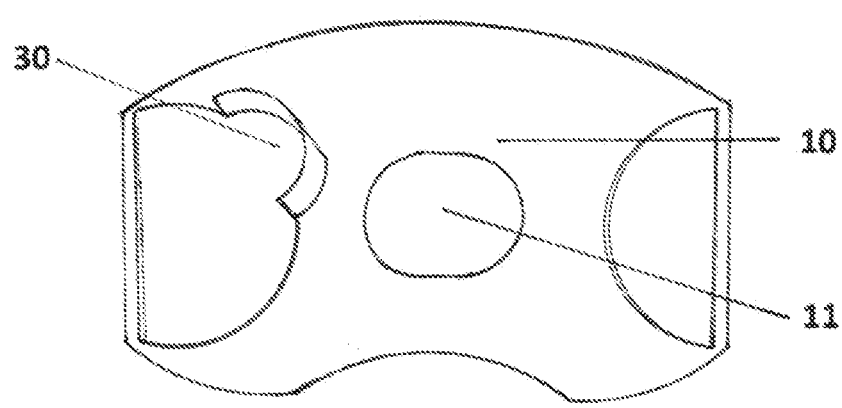

FIG. 5: Alternative Bite Block Design to latch other tubes.

DRAWINGS

Reference Numerals

10—Bite Block.
11—Proximal opening.
12—Introducer Body.
13—Introducer Extension.
14—Distal opening.
15—Introducer Extension tip.
16—Steel laminate distal tip bending.
17—Introducer Body 45 degree bending.
18—Elastomeric material proximal overlap into distal opening.
19—Elastomeric material Introducer Extension tip overlap.
20—Steel laminate strip.
20a—Steel laminate strip extension.
21—Elastomeric material tube with detail.
21a—Elastomeric material covering steel strip extension.
22—Posterior Pharyngeal Wall.
23—Posterior Esophageal Wall.
24—Esophageal opening.
25—Trachea.

26—Glottis.
27—Epiglottis.
28—Interarythenoid notch.
29—Pyriform Sinus.
30.—Latch for endotracheal tube.

DETAILED DESCRIPTION OF THE INVENTION

The embodiment described in the present patent is composed of three elements depicted in FIGS. 1 and 2. A proximal rigid structure that is essentially a bite block 10. a well-known tool to people familiar with the art. It consists of a proximal opening 11, and a rigid tubular structure connected to the second component that is the fully collapsible introducer body 12. In addition, the third component or distal introducer extension 13, conformed by steel laminated strip extension 20a and elastomeric material covering the strip extension 21a.

Introducer body or tube 12 is composed of a semi rigid laminate strip 20 attached to the floor of elastomeric material tube 21 with a length of about 15 cm. The proximal end is connected to bite block 10 and proximal opening 11. It smoothly tapes towards distal opening 14. Its length can be modified when used for endoscopic procedures that require repeated passages of the endoscope. For this purpose a length of 25 cm is recommended. FIG. 2a shows semi rigid laminate strip 20 at the bottom of introducer tube 12 after cutting a section of elastomeric material 21.

The purpose of semi rigid laminate 20, is to give structural stiffness to introducer body 12 during the insertion process, and during the passage of medical probes in their way to the esophagus. Steel laminate with a thickness of about 0.020" and a width of about 0.5" seem to fulfill the need of stiffness and flexibility to follow the anatomical curvatures during the insertion process.

The thickness and young modulus of fully collapsible elastomeric material tube 12, should be such to allow some deformation during the passage of the probe, but still be able to maintain a tubular conduit shape. Minimizing pressure and friction against the adjacent mucosa. Nitrile rubber with a thickness of 0.031" and a durometer of 60 seems to meet these requirements. Different materials like latex of silicone can be used as elastomeric elements but nitrile seems to have the best tensile strength and elasticity at a durometer of 60 and thickness of 0.031 inches with a much smaller profile not to mention the absence of allergenic properties. The friction over the surface of the white nitrile is reduced by the use of a dry lubricant like Duraglide R, additional lubricant like silicone based one can also be used. Prior to the insertion of the medical probe ultrasound gel filling the tube lumen, will give a third layer of lubricity to the passage of the medical probe.

FIGS. 2b and 2c depicts in detail the third component or distal introducer extension 13. This is a continuation of steel laminate 20 forming steel strip extension 20a. Comprises of, approximately 3 cm of steel strip 20a. This is covered by elastomeric material 21a that overlaps the distal end of laminated strip 19. The purpose of distal overlap 19, and bending of steel laminate end 16, is to increase the tip's surface and its compliance. This tip will make initial contact with pharyngeal mucosa 22 and then will slide onto posterior esophageal wall 23 as is seen in FIG. 3a 3b. Elastomeric material 21a extents 5 mm proximally inside introducer tube 18. This will help to keep distal opening 14 flattened, smoothing out the transition from distal tip 15 to elastomeric tube 12. The flattening of the distal opening is facilitated by thinning the distal edges of elastomeric material 12a.

The length of the introducer from the bite block to its distal tip is about 16-17 cm. other embodiments claim the need for a length of at least 20 cm for esophageal introducers. However, to ensure an uninterrupted passage of an esophageal probe, distal opening 14, just needs to be at about behind the interarythenoid notch 28. At this level, once the medical device exits distal opening 14, it will find a straight vertical passage into esophagus. Introducer extension 13 and posterior esophageal wall 23, will shape the conduit following distal opening 14 as shown in FIG. 3c. This arrangement will prevent any possible anterior displacement into glottis 26 or even trachea 25. If the embodiment is to be tried in pediatric patients, then the dimensions should be tailored accordingly.

The design of the introducer was based on the anatomical considerations of the oropharyngeal structures. Previous assemblies did not take in to consideration the crucial fact that esophageal opening 24 at the level of glottis 26 is mostly a virtual space, FIG. 4. Therefore, since esophageal opening 24 is a slit like virtual space, the best design that would better negotiate through this space, with minimal trauma, would be a thin strip element. Introducer extension tip 15 has this particular feature. It slides effortlessly into the esophagus as shown in FIGS. 3a to 3c.

Alternative Embodiments

Steel laminate 20 may be modified to increased thickness to provide more consistency that may be needed in condition where the neck cannot be hyperextended or there is crowding of devices in the oral cavity like in trauma patients.

Elastomeric tube 20, may be extended all the way to the tip of introducer extension 13. The edges should be thinned out assiduously to avoid scratching of the mucosal surfaces.

In cases in which the neck cannot be extended a superior location of the steel laminate 20, instead of an inferior placement as described above may facilitate the advancement of a medical device by providing a hard surface to push against during the introduction.

The bite block design can be modified to accommodate other tubes and catheters that may be used concomitantly. FIG. 5 This can be done by extending the wings on the sides and adding latches for other tubes or probes in use. Also if the device is used for gastric interventions the use of an attachment to proximal end 11 that contains a valve and a connection to insufflate air can be used.

Method of Use and Advantages

The utilization of this embodiment greatly facilitates the process of reaching esophageal opening 24. The handling of the introducer is made quite easy by holding the proximal end that is indeed a bite block 10, a device commonly used in the trade. Prior to the insertion, the collapsed introducer body 12 is angulated about 20-30 degrees mid-way 17. Then, it is introduced in the midline of the throat and then gently pushed on posterior pharyngeal wall 22, always maintaining the mid line position FIG. 1a. Introducer extension tip 15, will come in contact with the pharyngeal mucosa 22, below the upper level of the posterior tongue beyond the line of sight, FIG. 3a. In the absence of any anatomical deformities that would otherwise be evident by simple visual inspection or by history, further pressure in bite block 10 will inevitably advance introducer extension tip 15, into esophageal opening 24, FIG. 3b, FIG. 3c. Another particular advantage of this embodiment is its high flexibility, since the pressure applied proximally will be buffered distally by the bending of introducer tube 12 minimizing the pressure against pharyngeal mucosa 23 as the tip slides into esophageal opening 24. Incidentally, the current standard of care is an essentially blind introduction of esophageal probes by observing the endoscope only up to the level of the throat, or the upper level of the posterior tongue. However, in the case of TEE probes, by design the distal 7 cm harbors the ultrasound crystals and the mechanical components, therefore is rigid and thick. This feature makes the passage into esophageal opening 24, quite challenging. Furthermore, by design the distal end of the transesophageal probe hinges in multiple directions. This makes the guidance before entering the esophagus even more difficult, with the need to reorient the probe as needed, many times with the operator fingers.

If the maneuver is done with a bite block already in place, then the manipulation of the endoscope or probe is done completely blind.

Misplacement or bending of the probe will not be recognized except by the inability to advance it upon further pressure.

This esophageal introducer departs from prior attempts in the art to create a facilitator to pass medical devices into the esophagus more specifically trans esophageal probes. A fully collapsible elastomeric material tube, without any radial strength 21 and steel laminate 20 with minimal volume allow this introducer to have a minimal cross sectional area in contrast to previous attempted devices. Its malleability and the softness of the elastomeric material make it the most gentler to the mucosal surface.

Introducer extension 13, was designed to effortlessly negotiate down posterior pharyngeal wall 22 and slide into esophageal opening 24, FIG. 4; without the need for visual endoscopes or more sophisticated devices. Its construction is simple, its use easy and its cost economical.

Once the introducer has been advanced into the esophagus, the patient is still able to talk and relate any discomfort; the easiness of the passage of the device obviates the needs for deeper levels of sedation that increases the risk of the procedure. Even more, in completely sedated or under general anesthesia patients its use is quite convenient since patient participation is not required.

Prior to positioning the embodiment in place, the lumen of the elastomeric tube is generously lubricated with ultrasound gel. Then the tee probe or gi endoscope is introduced. The former has the disadvantageous construction with 7 cm of a stiff distal end that makes difficult the negotiation of the angulation between the floor of the mouth and the pharynx. This process is helped by 2 maneuvers. A simple elevation of the chin by 30 degrees and elevation of the head to get a sniffing position. This will reduce the anatomical curvature from 90 to about 60 degrees FIG. 3d facilitating the advancement of the distal end. Another maneuver is to pull back the bite block 1-2 cm proximally when resistance to passage is found, then the probe is advanced 1-2 cm; and subsequently both are advanced together into the esophagus.

What is claimed:

1. An article of medical use being an esophageal introducer to facilitate the passage of medical instruments form the mouth into the esophagus that comprises:
    (a) an elongated, fully collapsible within the anatomical boundaries of use introducer tube made with means for structural consistency along a bottom of said introducer tube, said introducer tube having a proximal end, a distal end, and a lumen extending between; said introducer tube having a predetermined internal diameter large enough to allow medical instruments to pass unobstructed through a length thereof, said length enough to traverse the distance from the mouth incisors line to the esophageal opening;
    (b) a bite block attached to the proximal end of said fully collapsible introducer tube; and
    (c) a distal extension of the introducer tube having a flat, tapered shape of a predetermined length that is a continuation of said bottom of the introducer tube with means for structural consistency.

2. The introducer assembly of claim 1 wherein said collapsible introducer tube is made of elastomeric material able to completely collapse during introduction into the pharynx and stretch out during passage of medical probes into the esophagus.

3. The introducer assembly of claim 2 wherein said assembly is made of a high tensile elastomer like nitrile rubber.

4. The introducer assembly of claim 2 wherein said collapsible introducer tube tapers from said proximal end to said distal end.

5. The introducer assembly of claim 2 wherein said distal end of the introducer tube includes edges that are beveled or thinned out.

6. The introducer assembly of claim 2 wherein said elastomeric material has a durometer of about 60 Shore A or less.

7. The introducer assembly of claim 2 wherein the inner surface of said collapsible introducer tube is covered by dry lubricant and viscous lubricant.

8. The introducer assembly of claim 1 wherein the means for providing structural consistency further comprises a steel laminate of flexible material with enough rigidity to maintain said structural consistency.

9. The introducer assembly of claim 8 wherein said steel laminate is attached at the bottom of the introducer tube and has a thickness of approximate 0.018 in.

10. The introducer assembly of claim 1 wherein said distal extension is comprised of a continuation of said steel laminate at the bottom of said elastomeric collapsible introducer tube as a means for structural consistency.

11. The introducer assembly of claim 8 wherein said steel laminate has a tapered shape towards a distal end thereof.

12. The introducer assembly of claim 7 wherein said steel laminate is covered by elastomeric material overlapping the edges thereof, thereby providing non traumatic contact surfaces with tissue.

13. The introducer assembly of claim 1 wherein a distal 3 mm of said steel laminate angulates 45 degrees.

14. The introducer assembly as in claim 1 wherein said elastomeric introducer tube is bent about 20-30 degrees in the proximal portion thereof prior to the introduction into the esophagus.

15. The introducer assembly of claim 1 wherein the length of said introducer is extended to about 25 cm for esophageal or gastric interventions to be used as an overtube.

16. A method for introducing a medical instrument, in particular a tee probe, or an endoscope, into the esophagus, through the esophageal introducer of claim 1 that comprises:
    providing said esophageal introducer comprising of a bite block, a fully collapsible introducer tube and a distal extension,
    providing a steel laminate attached at the bottom of said fully collapsible introducer tube as a means for structural consistency with a tapered distal end extending into said distal extension, allowing the introducer tube to maintain a consistent structure allowing for manipulation of said fully collapsible introducer tube and distal extension from said proximal end during advancement of said distal extension into an esophageal opening and afford stable consistency during esophageal probe passage;

providing a fully collapsible elastomeric tube of predetermined diameter able to accommodate most esophageal probes;

providing 20 to 30 degree angulation to mid-section of said elastomeric tube prior to insertion into mouth cavity;

filling said fully collapsible introducer tube with ultrasound gel through said proximal end to provide with another layer of lubricity;

advancing said introducer through the mouth till said distal extension tip reaches posterior pharyngeal wall holding proximally said bite block; and further pressing proximally on said bite block, allowing said tip of distal extension to slide down the posterior pharyngeal wall into esophageal opening.

17. The method of claim 16 further comprising the step of hyperextending the neck while elevating the head in a sniffing position in order to decrease the angulation between the floor of the mouth and the pharynx.

18. The method of claim 17 further comprising the step of introducing an esophageal probe or other medical instrument into the esophagus while maintaining the neck in hyperextension.

19. The method of claim 16 further comprising the step of facilitating the passage of a medical probe through the angulation between the mouth floor and pharynx when the probe cannot negotiate the throat angulation when patients cannot hyperextend the neck, consisting of pulling out said introducer an inch and advancing the probe an inch into said fully collapsible introducer tube, then advancing the probe and said introducer together until the throat angulation is negotiated.

* * * * *